United States Patent [19]

Harada

[11] 4,205,192
[45] May 27, 1980

[54] PROCESS FOR PRODUCING 5-ALKYLIDENENORBORNENE

[75] Inventor: Tetsuya Harada, Tokyo, Japan

[73] Assignee: Japan Synthetic Rubber Company, Limited, Tokyo, Japan

[21] Appl. No.: 945,348

[22] Filed: Sep. 25, 1978

[30] Foreign Application Priority Data

Mar. 31, 1977 [JP] Japan ................................. 52-35437

[51] Int. Cl.$^2$ ............................................ C07C 13/28
[52] U.S. Cl. .................................................. 585/363
[58] Field of Search .................... 260/666 PY, 666 A; 585/363

[56] References Cited

U.S. PATENT DOCUMENTS 3,347,944  10/1967  Fritz et al. ............................ 585/363

FOREIGN PATENT DOCUMENTS 50-35072 11/1975 Japan .
1111924 5/1966 United Kingdom .
1335138 10/1973 United Kingdom .

OTHER PUBLICATIONS

Encyclopedia of Chemical Technology 18, 541.

Primary Examiner—Veronica O'Keefe
Attorney, Agent, or Firm—Oblon, Fisher, Spivak, McClelland & Maier

[57] ABSTRACT

A process for producing a 5-alkylidenenorbornene, which comprises subjecting a 5-alkenylnorbornene to catalytic reaction in the presence of ammonia and at least one alkali metal hydride selected from the group consisting of lithium, sodium and potassium hydrides. By using said alkali metal hydride supported on a carrier, the above-noted isomerization can be efficiently carried out with a relatively small amount of the catalyst.

12 Claims, No Drawings

PROCESS FOR PRODUCING 5-ALKYLIDENENORBORNENE

BACKGROUND OF THE INVENTION

1. Field of the Invention

This invention relates to a process for producing a 5-alkylidenenorbornene by the isomerization of a 5-alkenylnorbornene.

2. Description of the Prior Art

5-Alkylidenenorbornenes are industrially important diene monomers as the third components of ethylene-propylene-diene rubbers (hereinafter referred to as EPDM). Above all, 5-ethylidenenorbornene (hereinafter referred to as ENB) is most widely used.

The production of ENB by the isomerization of 5-vinylnorbornene (hereinafter referred to as VNB), which is obtained by the Diels-Alder reaction from butadiene-1,3 and cyclopentadiene, is commerically advantageous because of easy availability and inexpensiveness of the starting materials. The isomerization of VNB can be effected by contacting with either acidic or basic reagent. However, since the acidic reagent does not give a good yield of ENB owing to partial polymerization and the like, a basic reagent is used in many cases. For instance, there is known a process in which VNB is contacted with (a) an alkali metal supported on a carrier, (b) a mixture of a strong base of an alkali metal and a polar organic solvent, or (c) a mixture of an alkali metal amide and a nitrogen-containing base (British Pat. No. 1,111,924). However, in view of disaster prevention, direct use of an alkali metal such as sodium, potassium or lithium in this method has a disadvantage of dangerous handlings.

In another known method, the isomerization of VNB into ENB is effected in the presence of a ternary system catalyst comprising an alkali metal or a complex thereof with ammonia, a carrier having a large surface area, and a compound of an alkali metal or alkaline earth metal (British Pat. No. 1,335,138). However, in this method too, there is a danger associated with the use of an alkali method as in the above method. Further, the procedure of supporting an alkali metal is troublesome and dangerous and a complex of an alkali metal with ammonia such as sodium amide is expensive.

In order to eliminate the above disadvantages, methods have been proposed for isomerizing VNB into ENB by contacting VNB with a mixture of an alkali metal hydride and dimethyl sulfoxide (Japanese Patent Publication No. 24,388/73) or a mixture of an alkali metal hydride and an aliphatic amine (Japanese Patent Publication No, 35,072/75). These methods provide an improvement in the conventional methods by utilizing an alkali metal hydride which is available at low cost and can be handled with relative easiness. These methods, however, have drawbacks in that they require a large quantity of comparatively expensive dimethyl sulfoxide or aliphatic amines and the repeated use of the catalyst is difficult because of the solubility of the catalyst in these reagents. A further disadvantage is a considerably high cost of recovering the reagent if an aliphatic amine having a boiling point relatively close to that of VNB or ENB is used.

In other methods than the above-mentioned methods of isomerization with alkali metals, there is used as catalyst a metal pentacarbonyl (Japanese Patent Publications Nos. 23,337/70 and 24,478/74) or a combination of an organic alkali metal compound and a polyamine (Japanese Patent Publication No. 40,469/74). Such a method has a disadvantage of high cost of the catalyst and, hence, of the isomerization.

SUMMARY OF THE INVENTION

An object of this invention is to provide a process for producing a 5-alkylidenenorbornene, which is free from the aforementioned disadvantages.

Another object of this invention is to provide a process for producing ENB from VNB with a high conversion and a high selectivity.

Other objects and advantages of this invention become apparent from the following description.

According to this invention, there is provided a process for producing a 5-alkylidenenorbornene, which comprises subjecting a 5-alkenylnorbornene to catalytic reaction by contacting it with at least one alkali metal hydride selected from the group consisting of lithium, sodium and potassium hydrides in the presence of ammonia.

DETAILED DESCRIPTION OF THE INVENTION

The process of this invention is quite a novel isomerization process free from the aforementioned disadvantages of the conventional methods and capable of producing ENB from VNB with a high conversion and a high selectivity by using as catalyst a mixture of an alkali metal hydride which is safe in handling and ammonia which is easily separated from VNB and ENB, both catalyst components being easily available from the market at low cost.

In practicing this invention, by using ammonia and a solid catalyst consisting of an alkali metal hydride supported on a carrier, it is possible to achieve efficient isomerization even in a relatively small amount of the catalyst. Since an alkali metal hydride is insoluble in ammonia and a hydrocarbon, the alkali metal hydride or a solid catalyst consisting of an alkali metal hydride supported on a carrier can easily be separated from the reaction mixture by a simple physical operation such as filtration or the like and then used repeatedly. Therefore, the process of this invention is particularly advantageous in industry.

Typical examples of the isomerization of 5-alkenylnorbornenes into 5-alkylidenenorbornenes according to this invention include, beside VNB into ENB, 5-propenylnorbornene into 5-propylidenenorbornene, 5-butenylnorbornene into 5-butylidenenorbornene, and 5-vinyl-6-methylnorbornene into 5-ethylidene-6-methylnorbornene.

The alkali metal hydride used in the process of this invention is at least one alkali metal hydride selected from the group consisting of potassium, sodium and lithium hydrides. The isomerization activity is in the order of potassium hydride > sodium hydride > lithium hydride. Although potassium hydride is the most active, the difference in activity between potassium hydride and sodium hydride is not so great, whereas the activity of lithium hydride is about a half of sodium hydride. The alkali metal hydride can easily be prepared on a commercial scale by hydrogenating an alkali metal dispersed in a hydrocarbon such as benzene, hexane, kerosene or the like and is commercially available in the form of powder containing a hydrocarbon.

The carrier used to support an alkali metal hydride is a porous material such as, for example, alumina, silica gel, aluminum silicate, activated carbon, ion-exchange resin or the like. A metal aluminosilicate such as a molecular sieve, synthetic or natural mica, or the like may also be used. It is preferable that the carrier has a surface area of 10 m$^2$/g or more.

The alkali metal hydride is supported on the carrier by either covering the carrier with a powdered alkali metal hydride or supporting a fused alkali metal on a carrier followed by hydrogenating the metal with hydrogen. It is also possible to support the hydride on a carrier by adding separately the carrier and a powdered alkali metal hydride to a mixture of ammonia and a 5-alkenylnorbornene and stirring the same vigorously.

The VNB prepared by Diels-Alder reaction from butadiene-1,3 and cyclopentadiene contains the endo form and the exo form. Some conventional catalysts exert unequal influence on susceptibilities of both forms to isomerization, whereas the catalyst of this invention does not preferentially affect the reactivity of one or the other form, and both forms are equally and easily isomerized into ENB. This is one of the features of this invention.

The process of this invention can be carried out by adding ammonia and an alkali metal hydride to a 5-alkenylnorbornene such as VNB. However, since the alkali metal hydride is scarcely soluble in the 5-alkenylnorbornene and ammonia, the reactant mixture must be kept in dispersion by vigorous agitation. When an alkali metal hydride supported on a carrier is used, a mixture of ammonia and a 5-alkenylnorbornene such as VNB is passed in liquid phase through a reactor packed with the solid supported catalyst, or alternatively, the solid supported catalyst is added to said mixture and agitated.

The amount of the catalyst added is subject to no particular restriction, but it is generally 0.1 to 20%, preferably 0.2 to 6%, by weight based on the weight of 5-alkenylnorbornene. The amount of ammonia added is also subject to no restriction, but its suitable amount is ⅓ to 2 times the weight of 5-alkenylnorbornene. When the carrier is used, it is preferable that the amount of the alkali metal hydride supported on the carrier is preferably 5 to 100% by weight based on the weight of the carrier, though it is not restrictive.

The reaction temperature is not critical and the reaction proceeds at room temperature. However, at higher temperatures, the reaction proceeds more smoothly and more rapidly, and both the conversion of 5-alkenylnorbornene and the concentration of the resulting 5-alkylidenenorbornene in the reaction mixture are higher. Because of a small difference in boiling point between the alkylidenenorbornene and the alkenylnorbornene, a higher concentration of the former is desired for the purification. In view of this, a suitable reaction temperature is generally 100° to 160° C., preferably 135° to 145° C. If the reaction temperature exceeds 160° C., although the rate of isomerization is increased, there is a possibility of formation of tetrahydroindene (hereinafter referred to as THI) by the Cope rearrangement. Since, at a temperature lower than 145° C., the rate of the Cope rearrangement is neglibible as compared with the rate of isomerization, a reaction temperature of 135° to 145° C. is preferred. At such a temperature, the reaction is completed in several minutes to several hours. The reaction pressure is such that the reaction system can be kept in liquid phase at such a reaction temperature.

In the case where the fixed bed catalyst is not used, the solid supported catalyst is easily recovered from the reaction mixture by physical procedures such as decantation, filtration, centrifugation and the like and recycled to the reaction system for reuse. In recycling, a fresh alkali metal hydride can be additionally supported or resupported on the solid supported catalyst, resulting in a reduction in catalyst cost. Therefore, this procedure is advantageous in industry.

Under the aforementioned conditions for carrying out the process of this invention, the starting material, i.e. a 5-alkenylnorbornene, is isomerized with a high selectivity to a 5-alkylidenenorbornene containing negligibly small amounts of by-products which, on purification, can easily be removed. The ammonia used in the isomerization can easily be recovered by distillation from the reaction mixture from which the catalyst has been separated, and the thus recovered ammonia can be recycled to the reaction system. The reaction mixture from which the catalyst and ammonia have been separated is a mixture comprising a 5-alkylidenenorbornene and an unreacted 5-alkenylnorbornene as major components. This mixture can be purified by a conventional treatment such as distillation or extraction to obtain a high-purity 5-alkylidenenorbornene.

The by-products formed in small amounts in the isomerization of a 5-alkenylnorbornene such as VNB into a 5-alkylidenenorbornene such as ENB include THI formed by the Cope rearrangement of VNB and a partially hydrogenated product of the norbornene ring. As mentioned before, the formation of the by-product THI can be minimized by suitable selection of the reaction temperature. Although some differences are seen in hydrogenation of a norbornene ring depending upon the presence or absence of a carrier the amount of norbornene-ring hydrogenated product is negligible, unless an alkali metal hydride catalyst is used in an excessively large proportion to the starting material such as VNB.

In the process of this invention, it is not necessary to use a high-purity 5-alkenylnorbornene such as purified VNB. As an example, a crude dimer fraction containing VNB and the like obtained by the reaction of impure butadiene-1,3 and impure cyclopentadiene can be used, without purification, as the starting material of isomerization. This is also one of the features of this invention.

DESCRIPTION OF PREFERRED EMBODIMENT

The invention is illustrated below in detail with reference to Examples which, however, are merely illustrative and not limitative.

Example 1

Into a 200-ml autoclave provided with an electromagnetic stirrer were charged VNB and ammonia in amounts as shown in Table 1 and a powdered alkali metal hydride as shown in Table 1, containing kerosen in the same weight as the hydride and, if necessary, a carrier as shown in Table 1. The resulting mixture was allowed to react at a predetermined reaction temperature for a predetermined reaction time. After the completion of the reaction, the reaction mixture was separated from the catalyst by decantation or filtration and analyzed by gas chromatography. The results obtained are shown in Table 1. The results indicate the following facts:

No isomerization into ENB occurs with an alkali metal hydride alone, regardless of the presence or absence of a carrier (No. 1 and No. 2), whereas the isomerization takes place when ammonia is added.

The presence of a carrier facilitates the dispersion of the isomerization catalyst in the reaction system, and enables the reaction to proceed smoothly. γ-Alumina, a molecular sieve, an ion-exchange resin and activated carbon are all effective carriers. Such carriers are effective even when they are separately added without previously supporting the alkali metal hydride thereon.

Potassium, sodium and lithium hydrides are effective as alkali metal hydrides, and the isomerization activity thereof is in the order of K>Na>Li.

The reaction between the reaction temperature and the reaction time clarifies that the reaction proceeds effectively even at a temperature (40° C.) near room temperature, though a long reaction time is required (No. 15). If the reaction temperature exceeds 160° C., the rate of rearrangement into THI is increased, though the rate of isomerization into ENB is increased (No. 12 and No. 13). Therefore, such high temperatures are not required.

No by-products (chiefly norbornene-ring hydrogenated products) other than THI are formed when the ratio of an alkali metal hydride to VNB is kept low.

The carrier and the catalyst may be separated from the reaction mixture by decantation and reused (No. 16).

Example 3

A supported catalyst was prepared by adding 10% of molten metallic sodium to powdered γ-alumina previously calcined at 600° C., and then hydrogenating the metallic sodium in a hydrogen stream at 200° C. for 7 hours. Using 5 g of the supported catalyst thus obtained, reaction was effected in the same manner as in Example 2. The analytical values of the reaction product were 2.7% of VNB and 97.3% of ENB.

The supported catalyst separated by decantation from the reaction mixture after the completion of the reaction was admixed with 20.0 g of VNB and 20 ml of ammonia. By using the supported catalyst thus treated, the above reaction was repeated. The analytical values of the reaction product were 2.4% of VNB and 97.6% of ENB.

Example 4

An equimolar mixture of butadiene-1,3 and cyclopentadiene was allowed to react in an autoclave at 165° C. for 3 hours. After the completion of the reaction, the reaction mixture was fractionated and the VNB fraction

Table 1

| | | Alkali metal hydride | | | | Reaction conditions | | | | Reaction Product Analysis (weight %) | | | |
|---|---|---|---|---|---|---|---|---|---|---|---|---|---|
| Run No. | Type of carrier | Amount of catalyst* (g) | Wt % based on VNB | Ammonia (ml) | VNB (g) | Amount of catalyst added (g) | Reaction temperature (°C.) | Reaction time (hour) | Pressure (kg/cm²) | VNB | ENB | THI | Others** |
| 1 | None | NaH 1.0 | 10.0 | — | 10.0 | — | 140 | 1.0 | 58 | 99.8 | — | — | 0.2 |
| 2 | γ-Alumina | NaH 1.0 | 10.0 | — | 10.0 | 3.0 | 140 | 1.0 | 57 | 99.8 | — | — | 0.2 |
| 3 | γ-Alumina | NaH 1.0 | 5.0 | 20.0 | 20.0 | 2.0 | 140 | 1.0 | 52 | 10.9 | 89.1 | 0.0 | 0.0 |
| 4 | Molecular sieve 4A | NaH 1.0 | 5.0 | 20.0 | 20.0 | 2.0 | 140 | 2.0 | 65 | 2.5 | 97.5 | 0.0 | 0.0 |
| 5 | " | NaH 1.0 | 5.0 | 20.0 | 20.0 | 2.0 | 100 | 2.0 | 47 | 13.8 | 86.1 | 0.0 | 0.1 |
| 6 | γ-Alumina | NaH 1.0 | 5.0 | 20.0 | 20.0 | 2.0 | 140 | 1.5 | 65 | 2.9 | 97.1 | 0.0 | 0.0 |
| 7 | Strongly basic anion exchange resin | NaH 1.0 | 5.0 | 20.0 | 20.0 | 1.0 | 140 | 1.5 | 64 | 2.4 | 97.6 | 0.0 | 0.0 |
| 8 | Activated carbon | NaH 1.0 | 5.0 | 20.0 | 20.0 | 1.0 | 140 | 1.5 | 64 | 3.1 | 96.9 | 0.0 | 0.0 |
| 9 | γ-Alumina | KH 1.0 | 5.0 | 20.0 | 20.0 | 2.0 | 140 | 1.0 | 66 | 2.6 | 97.4 | 0.0 | 0.0 |
| 10 | " | LiH 1.0 | 5.0 | 20.0 | 20.0 | 2.0 | 140 | 2.0 | 64 | 40.8 | 59.0 | 0.0 | 0.2 |
| 11 | " | NaH 1.0 | 5.0 | 20.0 | 20.0 | 2.0 | 145 | 1.0 | 76 | 6.0 | 94.0 | 0.0 | 0.0 |
| 12 | " | NaH 1.0 | 5.0 | 20.0 | 20.0 | 2.0 | 160 | 0.5 | 95 | 3.8 | 95.5 | 0.6 | 0.1 |
| 13 | " | NaH 1.0 | 5.0 | 20.0 | 20.0 | 2.0 | 170 | 0.5 | 112 | 1.8 | 96.0 | 2.0 | 0.2 |
| 14 | " | NaH 1.0 | 5.0 | 20.0 | 20.0 | 2.0 | 70 | 3.5 | 35 | 14.9 | 85.0 | 0.0 | 0.1 |
| 15 | " | NaH 1.0 | 5.0 | 20.0 | 20.0 | 2.0 | 40 | 7.0 | 14.0 | 12.9 | 87.0 | 0.0 | 0.1 |
| 16*** | " | NaH — | — | 20.0 | 20.0 | — | 140 | 1.5 | 52 | 6.1 | 93.9 | 0.0 | 0.0 |

Note:
*Contains kerosen in the same weight as that of the catalyst.
**Chiefly

***The catalyst separated by decantation from the reaction mixture of Run No. 6 was reused.

Example 2

Into the same 200-ml autoclave as in Example 1 were charged 20.0 g of VNB and 20 ml of ammonia. To the autoclave was added 5 g of a supported catalyst consisting of a predetermined amount of a powdered γ-alumina calcined at 600° C. covered with 20% by weight of a NaH-kerosene (50:50) powder. The resulting mixture was allowed to react at 140° C. for 1.5 hours. After the completion of the reaction, the reaction products were analyzed to find that there were 2.5% of VNB, 97.4% by ENB and 0.1% of others.

was analyzed by gas chromatography using Golay column Q-90 (0.25 mmφ×90 m) at 130° C. It was found that the endo-form content is 65% and the exo-form content is 35%.

In another run, an equimolar mixture of butadiene-1,3 and cyclopentadiene was allowed to react in an autoclave at 220° C. for 3 hours. The reaction mixture was fractionally distilled and the VNB fraction was analyzed in the same manner as mentioned above. It was found that the endo-form content is 5% and the exo-form content is 95%.

The two types of VNB obtained above were isomerized in the same manner as in Example 2. The results obtained are shown in Table 2.

Table 2

| In VNB | | Reaction product (%) | | | |
| --- | --- | --- | --- | --- | --- |
| Endo | Exo | VNB | ENB | THI | Others |
| 65% | 35% | 3.5 | 96.5 | 0.0 | 0.0 |
| 5% | 95% | 4.0 | 96.0 | 0.0 | 0.0 |

Example 5

In a manner similar to that in Example 2, 20.0 g of each of different 5-alkenylnorbornenes was isomerized. The results obtained are shown in Table 3.

Table 3

| | Reaction product (%) | | |
| --- | --- | --- | --- |
| 5-Alkenylnor-bornene charged | Unreacted 5-alkenyl-norbornene | 5-Alkylidene-norbornene | Others |
| 5-Propenyl-norbornene | 6.1 | (5-propylidene) 93.9 | 0.0 |
| 5-Vinyl-6-methyl-norbornene | 9.5 | (5-ethylidene-6-methyl) 90.5 | 0.0 |

Example 6

An isomerization test was effected using as the starting VNB a crude dimer fraction obtained by subjecting a crude $C_4$ fraction and crude dicyclopentadiene to Diels-Alder reaction. The composition of the crude dimer fraction used as the starting material was as follows:

| | |
| --- | --- |
| 4-Vinylcyclohexene (VCH) | 2.5% by weight |
| VNB | 41.6% by weight |
| Cyclooctadiene (COD) | 0.1% by weight |
| THI | 7.8% by weight |
| Dicyclopentadiene (DCP) | 48.0% by weight |

A stainless steel pipe of 1 inch in inner diameter and 400 mm in length was packed with γ-alumina powder (20 to 80 mesh (Tyler)) on which 20% by weight of sodium hydride based on the weight of the γ-alumina powder had been supported, and a mixture of the crude dimer fraction and ammonia (volume ratio: 10:1) was passed through the pipe at 135° C. at a liquid space velocity of 2.0. The result of the analysis of the reaction product was as follows:

| | |
| --- | --- |
| VCH | 2.5% by weight |
| VNB | 0.2% by weight |
| ENB | 41.2% by weight |
| COD | 0.1% by weight |
| THI | 7.9% by weight |
| DCP | 48.0% by weight |
| Others | 0.1% by weight |

From the above result, it can be seen that VNB can substantially completely be isomerized into ENB by passing the crude dimer fraction as the starting material through a fixed bed type reactor to effect the reaction.

What is claimed is:

1. A process for producing a 5-alkylidenenorbornene, which comprises:
    contacting a 5-alkenylnorbornene with a catalyst system of ammonia and at least one alkali metal hydride selected from the group consisting of lithium, sodium and potassium hydrides.
2. The process according to claim 1, wherein the alkali metal hydride is supported on a carrier.
3. The process according to claim 1 or 2, wherein the alkali metal hydride is potassium hydride or sodium hydride.
4. The process according to claim 2, wherein the carrier is alumina, silica gel, aluminum silicate, activated carbon, an ion-exchange resin, a molecular sieve, or a synthetic or natural mica.
5. The process according to claim 2, wherein the carrier is γ-alumina, a molecular sieve, a strongly basic anion-exchange resin, or activated carbon.
6. The process according to claim 1 or 2, wherein the 5-alkenylnorbornene is 5-vinylnorbornene.
7. The process according to claim 1 or 2, wherein the amount of the alkali metal hydride is 0.1 to 20% by weight based on the weight of 5-alkenylnorbornene.
8. The process according to claim 7, wherein the amount of ammonia is one-third to two times the weight of 5-alkenylnorbornene.
9. The process according to claim 8, wherein the reaction temperature is 100° to 160° C.
10. The process according to claim 6, wherein the reaction temperature is 135° to 145° C.
11. The process according to claim 9 or 10, wherein the reaction pressure is sufficiently high for keeping the reaction system in the liquid phase.
12. The process according to claim 11, wherein the reaction time is several minutes to several hours.

* * * * *